(12) United States Patent
Baldwin et al.

(10) Patent No.: US 8,386,194 B1
(45) Date of Patent: Feb. 26, 2013

(54) DETERMINING BOND SURFACE CONDITION IN COMPOSITE STRUCTURES

(75) Inventors: Joel P. Baldwin, Seattle, WA (US); Russell L. Keller, Maple Valley, WA (US); Eugene Dan-Jumbo, Bothell, WA (US)

(73) Assignee: The Boeing Company, Chicago, IL (US)

( * ) Notice: Subject to any disclaimer, the term of this patent is extended or adjusted under 35 U.S.C. 154(b) by 264 days.

(21) Appl. No.: 12/822,610

(22) Filed: Jun. 24, 2010

(51) Int. Cl.
*G01N 31/00* (2006.01)
*G01N 19/04* (2006.01)

(52) U.S. Cl. .......................................... 702/30; 73/150 A

(58) Field of Classification Search .................... 702/30; 73/150 A
See application file for complete search history.

(56) References Cited

PUBLICATIONS

Roger P. Woodward, "Prediction of Adhesion and Wetting from Lewis Acid Base Measurements",2000, First Ten Angstroms Inc, pp. 1-6.*
Finn Knut Hansen, "The Measurement of Surface Energy of Polymers by Means of Contact Angles of Liquids on Solid Surfaces", 2004, University of Olson, pp. 1-12.*
"Certification Testing Methodology for Composite Structures, vols. I and II" DOT/FAA/CT-86/39, Oct. 1986.
"Handbook: Manufacturing Advanced Composite Components for Airframes" DOT/FAA/AR-96/75, Apr. 1997.
"Advanced Certification Methodology for Composite Structures" DOT/FAA/AR-96/111, Apr. 1997.
"Effects of Surface Preparation on the Long-Term Durability of Adhesively Bonded Composite Joints" DOT/FAA/AR-03/53, Jul. 2003.
"Bonded Repair of Aircraft Composite Sandwich Structures," DOT/FAA/AR-03/74, Feb. 2004.
"Assessment of Industry Practices for Aircraft Bonded Joints and Structures," DOT/FAA/AR-05/13, Jul. 2005.
"Design of Durable, Repairable, and Maintainable Aircraft Composites," (SAE AE-27, 1997).
"The measurement of surface energy of polymer means of contact angles of liquid on solid structures, A short overview of frequently used methods by Finn Knut Hanson, Department of Chemistry, University of Oslo", 2004.
Dan-Jumbo et al., "Bond Surface Testing Apparatus and Method," USPTO U.S. Appl. No. 13/023,682, 29 pages.

* cited by examiner

*Primary Examiner* — Michael Nghiem
*Assistant Examiner* — Manuel Rivera Vargas
(74) *Attorney, Agent, or Firm* — Yee & Associates, P.C.

(57) ABSTRACT

The condition of a bond surface is determined. A 3-D wettability tension curve is generated for the bond surface which represents a range of possible wettings of an adhesive on the bond surface that may result in a bond joint of acceptable quality. At least three surface energies on the bond surface are measured, and the wettability curve is used to determine whether the condition of the bond surface is acceptable based on the measured bonding surface energies.

20 Claims, 5 Drawing Sheets

DETERMINING BOND SURFACE CONDITION IN COMPOSITE STRUCTURES

TECHNICAL FIELD

This disclosure generally relates to adhesive bonding, especially of composites, and deals more particularly with a method for determining the condition of a bond surface.

BACKGROUND

Structural bonds made with adhesives are used in various industries to fasten parts or structural elements together, or to rework structures. In the aircraft industry, for example, composite patches may be attached to exterior airframe skins in order to rework and/or strengthen sections of the skin. These patches may be adhesively bonded to the skin, however, another means may require the use of mechanical fasteners to attach the patch to the skin in addition to the adhesive in order to provide secondary load paths. In the past, adhesively bonded patches with fasteners may not be certified by certifying authorities because of less than desirable predictability of the strength and durability of the bonds.

The quality and durability of an adhesive bond joint may depend upon characteristics of the bond surface to which the adhesive is applied. The surface preparation required to achieve a good bond joint may be dependent upon tight process controls and the skill of the technicians who prepare the surface. Individual surface characterization techniques are available that provide information on a single surface variable, such as surface roughness or active functional groups using profilometry or X-ray photoelectron spectroscopy (XPS), respectively. However, both profilometry and XPS typically require measurements that require the parts to be transported to a measurement unit, rendering the inspection process impractical in the field, or in a manufacturing environment, due to the logistics of transporting the parts, and/or the time required to do so. None of the presently known techniques may be used to quantify and certify the condition of bond surfaces prior to the bonding process at a level that would aid in allowing confident prediction of long-term durability of the bond joint after it enters service.

Accordingly, there is a need for a method of determining bond surface condition that may be used to aid in predicting bond joint quality, particularly in composite structures. There is also a need for a method of determining bond surface condition that may be used in the field or in a production environment and which may aid in certifying of structural bonds joints that do not employ secondary mechanical fasteners. There is a further need for a method of determining bond surface condition using measured characteristics of a prepared bond surface which take into account potentially wide variations of the measured results on the bond surface.

SUMMARY

The disclosed embodiments provide a method of determining the condition of a bond surface that may aid in predicting bond joint quality, and which may be useful the certification of structural adhesive bond joints. The method provides: (1) a real time, on-airplane quantifiable three dimensional (3-D) surface energy measurement of a prepared bond surface, (2) a quantifiable standard for a prepared bond surface that has been certified, and (3) an analyzer tool and software that compares the real time measurement with predefined standards to determine when a prepared bond surface is acceptable. The method is based upon an assessment of the condition of the bond surface prior to the application of an adhesive. The condition of the bond surface is assessed by recording a 3-D information fingerprint of the bond surface which is then used to quantitatively determine whether the bond surface has been prepared in a manner that may ensure optimal bond-joint performance and long term in-service durability. The disclosed method provides quantifiable, traceable surface condition data along with acceptability criteria relating to the quality of a prepared surface. This quantified data provides a basis for assessing the condition of the bond surface and predicting the durability of the resulting bond joint which may allow certification of the bond joint and/or a repair patch. The method may reduce or eliminate subjectivity in assessing long term bond joint durability by comparing the quantified bond surface data to surface condition standards.

According to one disclosed embodiment, a method is provided of predicting the quality of an adhesive bond joint based on the condition of a bond surface. The method includes generating a 3-D wettability tension curve for the bond surface that represents a range of possible wettings of an adhesive on the bond surface that will result in a bond joint of acceptable quality. The method also includes measuring at least three surface energies on the bond surface related to the condition of the surface, and using the 3-D wettability curve to determine whether the condition of the bond surface will result in a bond joint of acceptable quality based on the measured bond surface energies. Measuring the bond surface energies may include placing at least three reference liquids on the bond surface, measuring the contact angle of each of the liquids placed on the bond surface, and deriving the surface energies from the contact angle measurements. Measuring the contact angles may be performed at multiple locations on the bond surface, using the same or different liquids. The liquids may be selected from the group consisting of: distilled water, dimethyl sulfoxide, diiodomethane, and ethylene glycol. Using the 3-D wettability curve may include determining whether the measured surface energies are within the wettability curve.

According to another disclosed embodiment, a method is provided of predicting the quality of a bond joint to be made on substrate surfaces using bonding adhesives. The method comprises selecting a substrate surface and an adhesive to be applied to the selected substrate surface for making a bond joint. A database of surface tension standards is generated for a plurality of combinations of adhesives and substrate surfaces. At least three reference liquids are placed on the selected substrate surface and the surface tension of each of the liquids is measured. The method further comprises selecting a surface tension standard for the database and comparing the measured surface tension with the selected surface tension standard. Generating the surface tension standards may include generating a 3-D wettability curve for each of the combinations of adhesives and substrate surfaces. Measuring surface tension includes placing at least three different reference liquids on the selected substrate surface and measuring the contact angle of each of the liquids on the selected substrate surface.

According to another embodiment, a method is provided of predicting the quality of a bond joint between an adhesive and the bond surface. The method comprises generating a database of bond surface characteristics representing acceptable bond joint quality standards for a plurality of combinations of adhesives and bond surfaces. The method also includes measuring at least one variable characteristic the bond surface indicative of the condition of the bond surface and comparing the measured characteristic to the database characteristics.

The method further comprises determining whether the bond surface may produce an acceptable bond joint based on the results the comparison. Generating the database includes determining for each of the combinations of bond surfaces and adhesives, the level of wetting of adhesive on the bond surface that produces acceptable bond joint quality. Measuring at least one variable characteristic of the bond surface may include placing three reference liquids on the bond surface, and measuring the contact angle between the liquids on the bond surface and the bond surface. Measuring the variable characteristic on the bond surface may include deriving three surface energies on the bond surface from the measured contact angles.

BRIEF DESCRIPTION OF THE ILLUSTRATIONS

DETAILED DESCRIPTION

Figure 1:
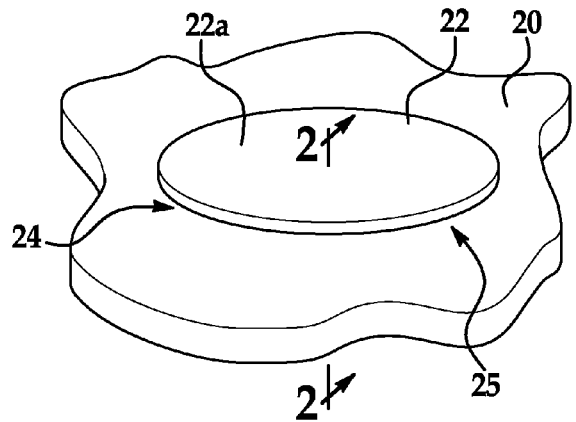
FIG. 1 is an illustration of an isometric view of a portion of a substrate surface having a patch adhesively bonded thereto.
Figure 2:
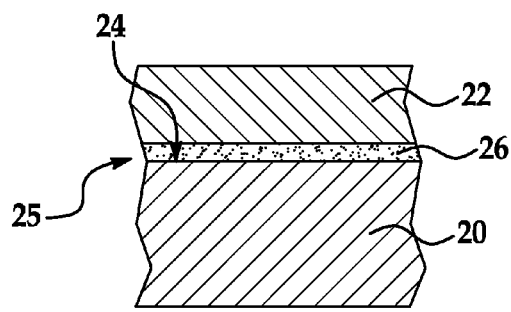
FIG. 2 is an illustration of a sectional view taken along the line 2-2 in FIG. 1.

Referring first to FIGS. 1 and 2, a patch 22 is bonded along a bond joint 25 by a layer of structural bonding adhesive 26 to the surface 24 of a substrate 20. The area of the substrate surface 24 where the bond joint 25 is to be made may sometimes be referred to herein as the bond surface 24. In the illustrated example, the patch 22 lies on top of the substrate surface 24, however in other examples the patch 22 may be recessed within the substrate so that the top surface 22a of the patch 22 lies substantially flush with the substrate surface 24. Both the substrate 20 and the patch 22 may be formed of composite materials, such as, for example and without limitation, carbon fiber epoxy. However, the disclosed method may be employed to determine the condition of a bond surface 24 where the substrate 20 and patch 22 comprise other materials, including but not limited to metals.

The bonding adhesive 26 may comprise any of various commercially available structural adhesives whose characteristics are well known. Prior to the application of a layer of adhesive 26 on the substrate surface 24, the surface 24 is prepared to receive the adhesive 26. This preparation may include, without limitation, cleaning, sanding, grinding, milling and/or removal of contaminates. The mechanisms by which an adhesive wets out on and adheres to a substrate surface are dependent on different forces on the surface. The major surface force components can be attributed to the work of adhesion $W_{12}$ between the two materials; the prepared surface (1) and a material (2) being bonded to it, where, $$W_{12} = \sum_{n=1}^{\infty} 2(\gamma_1^n \gamma_2^n)^{\frac{1}{2}}$$

in which $\gamma_1^n$ is the $n^{th}$ component surface energy of surface (1) and $\gamma_2^n$ is the $n^{th}$ component surface energy of material (2).

Figure 3:
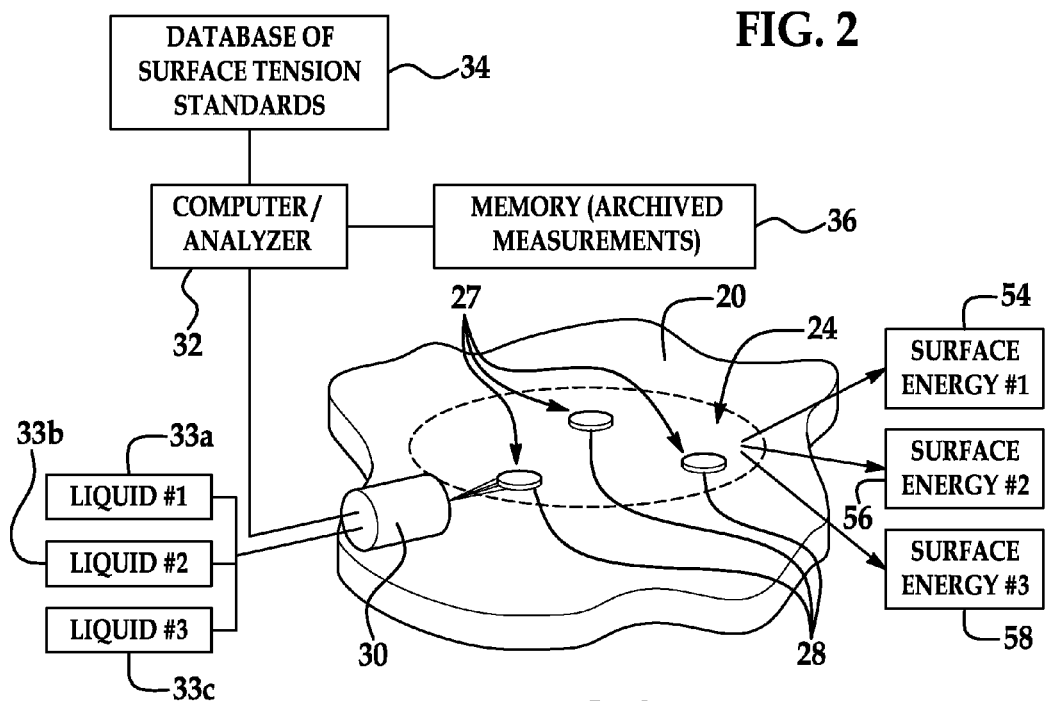
FIG. 3 is an illustration of a combined isometric view of the substrate and a block diagram of a system for performing substrate surface measurements.
Figure 4:
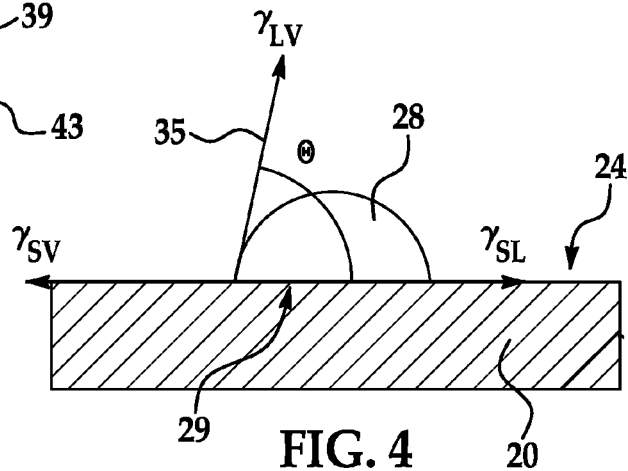
FIG. 4 is an illustration of a sectional view of a substrate showing a technique for measuring the contact angle of a droplet placed on the substrate.

In order to achieve acceptable bond joint 25 quality and ensure long term bond joint 25 durability, the substrate surface 24 should have characteristics which, although variable, fall within preselected ranges which are known to result in high quality, durable bond joints that meet application requirements, including certification requirements. Referring now to FIGS. 3 and 4, in order to determining whether the condition of a bond surface 24 is likely to result in an adhesive bond joint 25 of acceptable quality, certain characteristics of the surface 24 are measured and are compared with standards selected from a database 34, using a computer 32 or similar analyzer. In one embodiment, the measured characteristics may be combined and analyzed to determine the surface tension γ of reference liquids 33a, 33b, 33c that are applied to the substrate surface 24. These measured surface tensions γ are compared with the database 34 of surface tension standards to determine whether the condition of the substrate surface 24 is within limits that will result in adequate wetting of the adhesive on the substrate surface 24. A prediction of the quality of the bond joint 25 may be based on the degree of wetting of the adhesive on the substrate surface 24; higher levels of wetting may indicate a bond surface condition that will likely provide higher levels of bond joint 25 quality. The degree of adhesive wetting is a function of the surface energies 54, 56, 58 on the substrate surface 24, as will be discussed below. The surface energy measurements may be archived in a memory 36 or similar storage unit for future use, including use in certification of patches/bond joints 25.

As will be discussed below in more detail, in order to determine whether the surface characteristics fall within prescribed ranges, an information "fingerprint" of the substrate surface 24 is developed by placing droplets of at least three reference liquids 33a, 33b, 33c at specifically or randomly selected locations 27 on the substrate surface 24 where the bond joint 25 is to be made. In one embodiment, droplets 28 of three differing reference liquids 33a, 33b, 33c placed on the substrate surface 24 are used to respectively derive three differing surface energies 54, 56, 58 on the substrate surface 24, based on a measurement of the contact angle θ (FIG. 4) between a droplet 28 of each of the liquids 33a, 33b, 33c and the substrate surface 24. Suitable reference liquids 33a, 33b, 33c may include, for example and without limitation, distilled water, dimethyl sulfoxide (DMSO), diiodomethane, ethylene glycol and dimethyl formide. The technique used to place the droplets 28 may be selected such that the reference liquids 33a, 33b, 33c minimize contamination of the surface 24.

The contact angle θ may be measured using a measurement device 30 (FIG. 3) which may comprise a handheld tool that includes integrated means (not shown) for depositing the droplets 28 onto the surface 24, as well as means (not shown) for transferring the measurement data to the computer 32. It should be noted here that although it is possible to spot check the surface 24 at a single site using one droplet 28, placing droplets 28 at multiple locations 27 on the substrate surface 24 may increase the likelihood that the sampling process results in measurements that are representative of substantially the entire substrate surface 24 where the bond joint 25 is to occur.

Figure 3A:
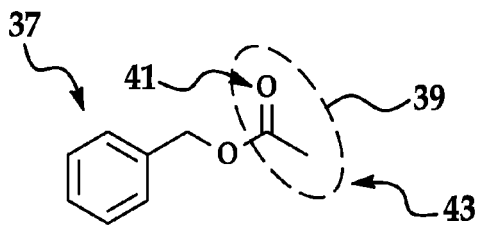
FIG. 3A is a schematic illustration of a chemical compound having two functional groups.

Referring to FIG. 3A, each of the reference liquids 33a, 33b, 33c placed on the substrate surface 24 reacts differently to identify special and different species on the substrate surface 24, sometimes referred to functional groups. FIG. 3A illustrates a chemical compound 37 having a functional group 39 defined by specific atoms 41 in a molecule 43. In organic chemistry, functional groups are specific groups of atoms within molecules that are responsible for the characteristic chemical reactions of those molecules. The same functional group 39 will undergo the same or similar chemical reaction(s) regardless of the size of the molecule of which it is a part. However, its relative reactivity can be modified by nearby functional groups. Thus, three reference liquids 33a, 33b, 33c may be used to respectively identify the three different surface functional groups. Each adhesive system and composite material has a unique functional group because of the polymer that makes up that particular material.

A determination of the condition of a bond surface may be made based on the identification of the functional groups 39. Identification of the functional groups 39 is the structural fingerprint of the substrate surface 24. The measurement process results in a fingerprint index number. If the measured index number is less than one, it indicates that complete wetting of the adhesive on the substrate surface may not be achieved.

As previously mentioned, a suitable measuring device 30 may be used to measure the contact angle θ between the droplet 28 and the substrate surface 24. The contact angle θ is measured between the outline tangent 35 of the droplet 28 at the contact location 29 and the substrate surface 24. The contact angle θ is essentially a measure of the ability of a liquid to spread or "wet-out" on a surface. The contact angle θ is also indicative of the affinity of a liquid to a solid surface and its measurement can be used to determine hysteresis between the advancing angle and the recessing angle of the droplet 28. At the interface between each liquid droplet 28 and the substrate surface 24, the function connecting the contact angle θ with the surface energy is expressed by Young's Equation:

$$\gamma_{SV} + \gamma_{SL} + \gamma_{LV} \cos \theta = 0$$

where,
$\gamma_{SL}$ is the solid-liquid interfacial tension,
$\gamma_{SV}(\gamma_S)$ is the solid-vapor interfacial tension, and
$\gamma_{LV}(\gamma_S)$ is the liquid-vapor interfacial tension.

Only $\gamma_{LV}$ and angle θ may be measured, consequently conditional equations are necessary to determine $\gamma_{SL}$ and $\gamma_{SV}$. Several models have been developed in the art to calculate these parameters, including the Newmann Model, the Owens & Went Model and the Good Van Oss Model. Each of these models has a dispersive component due to Lifshitz-Van der Walls interactions, and non-dispersive (polar) components comprising polar interactions. By depositing a droplet of three differing reference liquids 33a, 33b, 33c on a substrate surface 24 with known dispersive and polar components, i.e. known surface tensions γ, the energies 54, 56, 58 of the surface 24 may be calculated using the computer 32 or similar analyzer.

Figure 5:
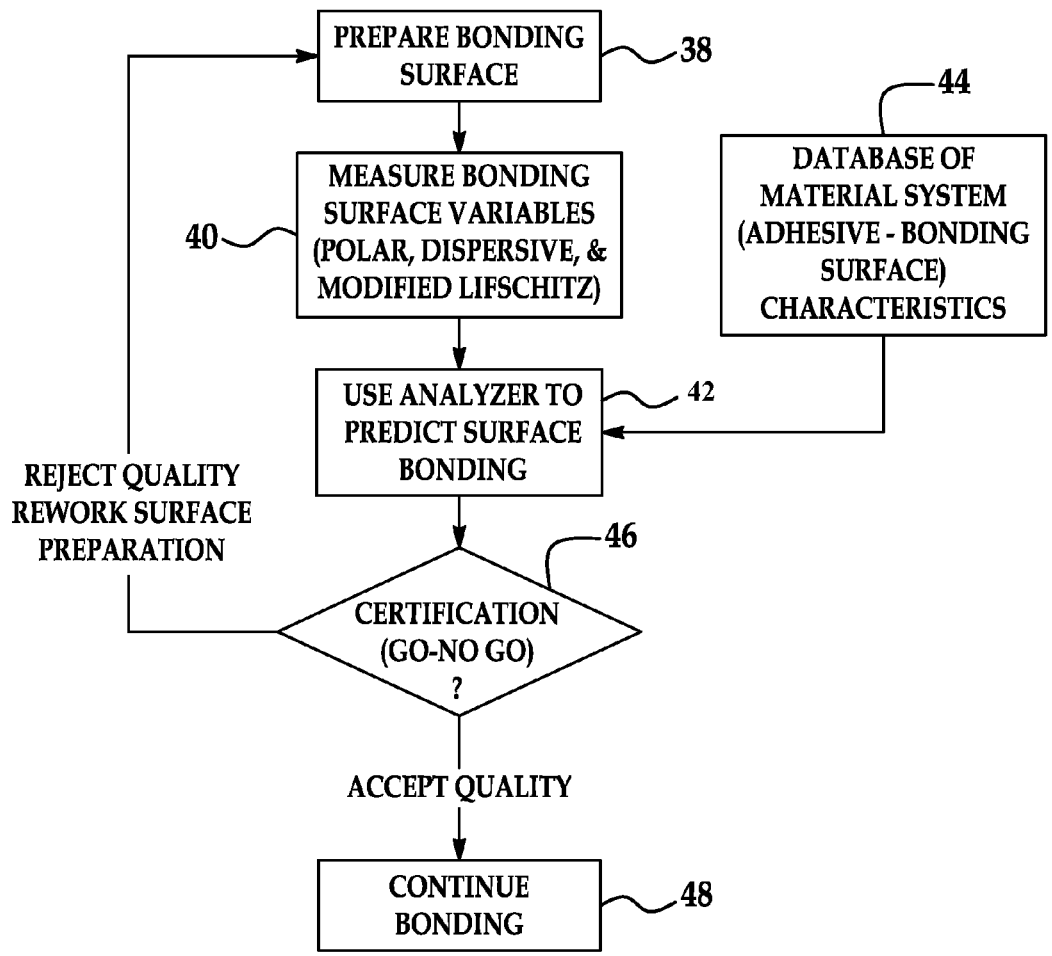
FIG. 5 is an illustration of a flow diagram of a method of determining the condition of a bond surface according to the disclosed embodiments.

Attention is now directed to FIG. 5 which illustrates the overall steps of a method of determining the condition of a bond surface 24, useful in predicting bond joint 25 quality, by determining the information fingerprint of the bond surface 24. At step 38, the bond surface 24 is prepared to receive the adhesive. This preparation may include, without limitation, grinding, trimming, sanding and cleaning the bond surface 24 with solvents or the like and/or other suitable means to remove contaminates or otherwise achieve desired surface characteristics. Next, at step 40, surface bond characteristics are measured which comprise variables such as the polar, dispersive and modified Lifschitz surface energies 54, 56, 58 respectively of the bond surface 24. The determination and use of the modified Lifschitz surface energy 58 (an acid-base force) of the bond surface 24 is useful in minimizing errors in bond surface measurements due to variations or deviations in the surface 24 that may occur substrate-to-substrate. The variable surface characteristics that are measured and the techniques for measuring them may be independent of the steps and processes that may be used in preparing the substrate surface in step 38.

At step 40, the three surface energies 54, 56, 58 of the bond surface are indirectly measured. These surface energies 54, 56, 58 are derived from measurements of the contact angles θ of three of the reference liquids 33a, 33b, 33c placed on the bond surface 24 at the same or at different locations 27. Based on the contact angles measurements, the computer 32 is used to derive the polar, dispersive and modified Lifschitz surface energy components 54, 56, 58 respectively which characterize the bond surface 24.

Figure 6:
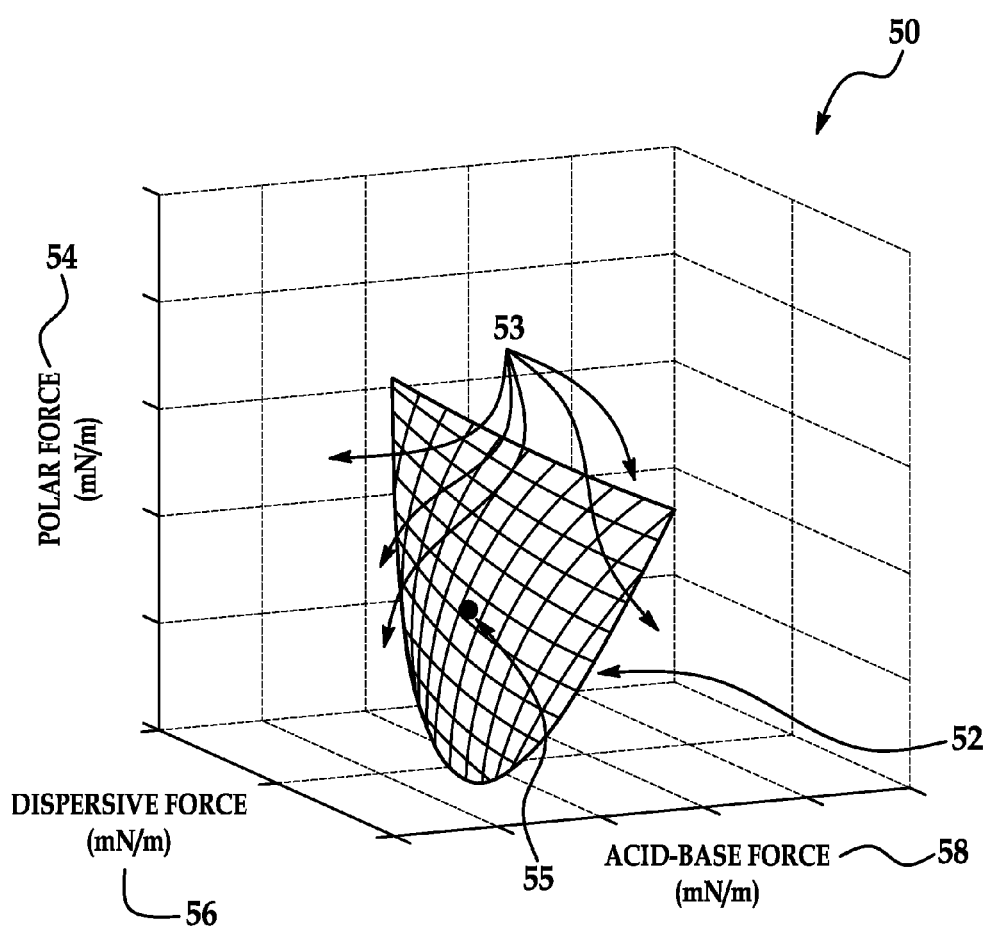
FIG. 6 is an illustration of a graph showing a 3-D wettability curve used in the method of determining the condition of a bond surface.

At step 44 a database 34 (FIG. 3) of material system characteristics is generated with surface tension standards 34 for each of a plurality of combinations of substrates 20 and adhesives 26. These surface tension standards 34 are generated by measuring the three surface energy components 54, 56, 58 (polar, dispersive and modified Lifschitz) of the various substrate surfaces 24 that are prepared under controlled and validated processes. The generation of the surface tension standards 34 involves placing droplets 28 of a plurality of reference liquids (not shown), for example, ten liquids, on the substrate surface 24 and measuring the contact angles θ for each of the liquids. The surface energies 54, 56, 58 for each of these contacts angles θ are then calculated, and a number of the reference liquids 33a, 33b, 33c, e.g. 3, are chosen that result in the highest surface energies 54, 56, 58. These same three reference liquids 33a, 33b, 33c are used in step 40. This database 34 of surface tension standards together with similar data describing the surface tension standards for the adhesives used with each of the substrates may be used to create a set of three dimensional wettability tension curves 52 for each substrate-adhesive combination. FIG. 6 is a three dimensional graph 50 illustrating a typical three dimensional wettability tension curve 52 that is plotted as a function of three surface energies, namely a polar force component 54, a dispersive force component 56, and a modified Lifschitz or acid-based force component 58.

At step 42 the computer 32 (FIG. 3) or a similar analyzer determines whether the measured surface energies 54, 56, 58 at step 40 fall within the acceptable ranges defined within the database 34. Specifically, a determination is made at 42 as to whether the measured surface tension γ defined by the three surface energies 54, 56, 58 falls within the standardized wettability curve 52 for the particular substrate-adhesive combination under investigation. This determination is made by calculating the intersection point 55 of the measured surface energies 54, 56, 58.

At step 46, a go, no-go certification decision is performed. If the three measured surface energies 54, 56, 58 intersect at a point 55 that falls within the wettability curve 52 for the particular substrate material-adhesive combination being investigated, then the bond joint 25 may be certified and bonding may continue at 48. If, however, the intersection point 55 falls outside 53 the wettability curve 52, then the condition of the bond surface 24 may be deemed to be unacceptable, and the bond surface may be reworked, following which the measurement and evaluation processes at steps 40, 42 and 46 are repeated.

Figure 7:
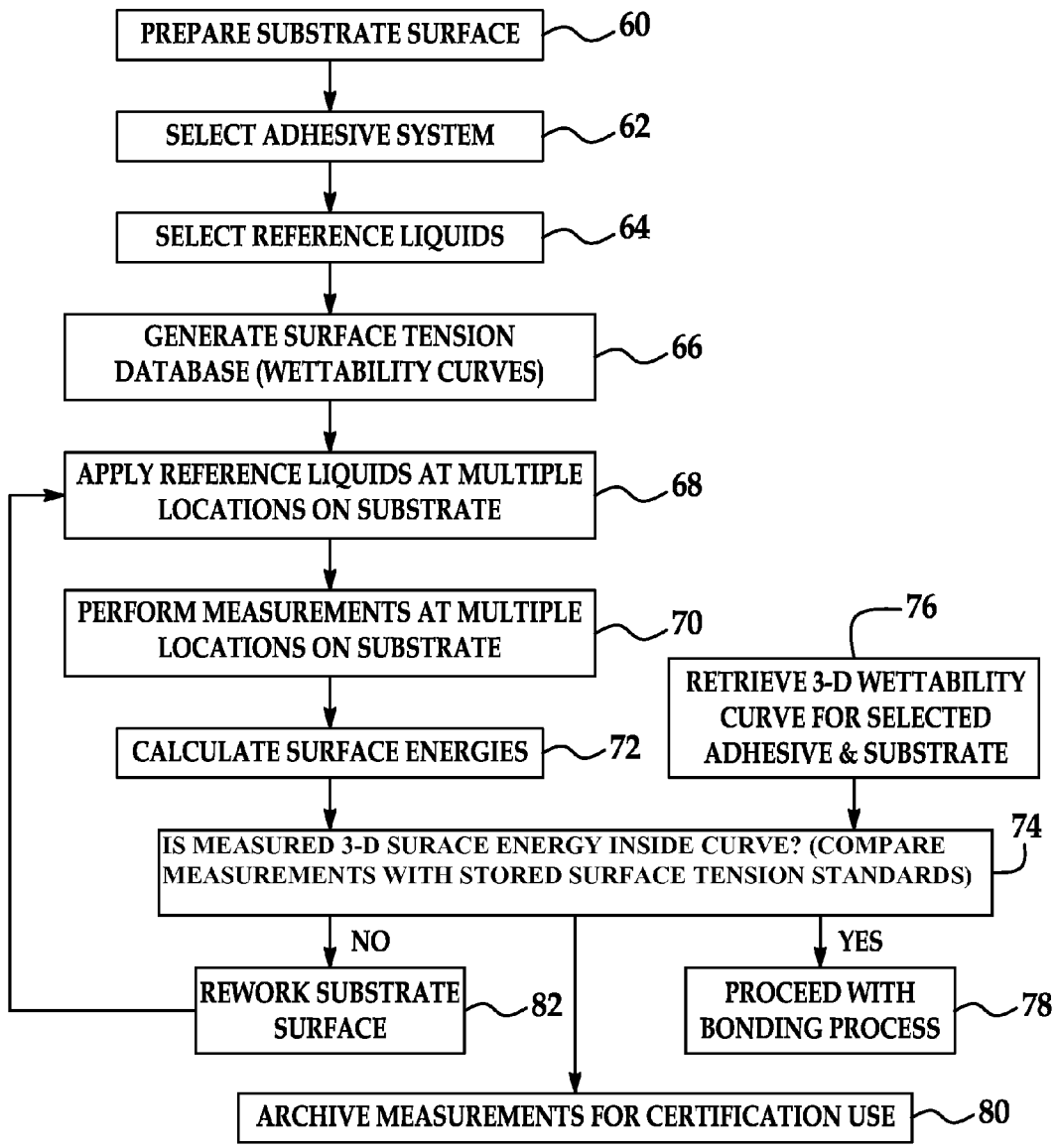
FIG. 7 is an illustration of a flow diagram showing additional details of the method of determining the condition of a bond surface.

FIG. 7 illustrates the steps of the method in greater detail. Beginning at step 60, the substrate surface 24 is prepared, as previously described. Next, at step 62, a particular adhesive 26 is selected for the substrate 24 on which the bond joint 25 is to be made. Next at 64, the reference liquids 33a, 33b, 33c are selected that are to be used to measure the surface energies 54, 56, 58. This step may involve using a plurality of reference liquids (not shown) and then selecting three of the liquids 33a, 33b, 33c that result in the highest calculated surface energies 54, 56, 58. At step 66, the database 34 is generated containing standardized surface tensions γ for each of a plurality of substrate-adhesive combinations. At step 68, the reference liquids are applied at multiple locations on the substrate. At step 70, measurements of the surface energies 54, 56, 58 are performed at multiple locations 27 on the substrate surface 24 using the three reference liquids 33a, 33b, 33c selected to generate the surface tension standards. These surface measurements are derived from measuring the contact angles θ of droplets 28 placed on the surface 24 as previously described.

Based on the contact angle θ measurements, the surface energies 54, 56, 58 can be calculated at step 72. At 76, the 3-D wettability curve 52 for the selected adhesive 26 and substrate 20 is retrieved. At step 74, the surface energies 54, 56, 58 derived from the contact angle θ measurement are plotted on the 3-D wettability curve 52 retrieved at step 76. If the plotted intersection 55 of the three surface energies 54, 56, 58 lies inside the retrieved wettability curve 52, then it may be predicted that the selected adhesive 26 will sufficiently wet-out on the substrate surface 24 to a degree that will result in a bond joint 25 of acceptable quality, in which case the bonding process may proceed at step 78. In effect, the three surface energies 54, 56, 58 derived from measurement of the contact angles θ indicates a level of surface tension γ of the applied adhesive 26 that is compared with a surface tension standard 34 represented by the wettability curve 52 retrieved at step 76. If, however, the intersection 55 of the plotted surface energies 54, 56, fall outside 53 of the retrieved wettability curve 52, then the substrate surface 24 may be reworked at 82, and steps 68-74 are repeated. The measured surface energies 54, 56, 58 and comparisons with the retrieved wettability curves 76 may be archived for future use, including use in certifying the bond joint, and for improving or altering the database 34.

Figure 8:
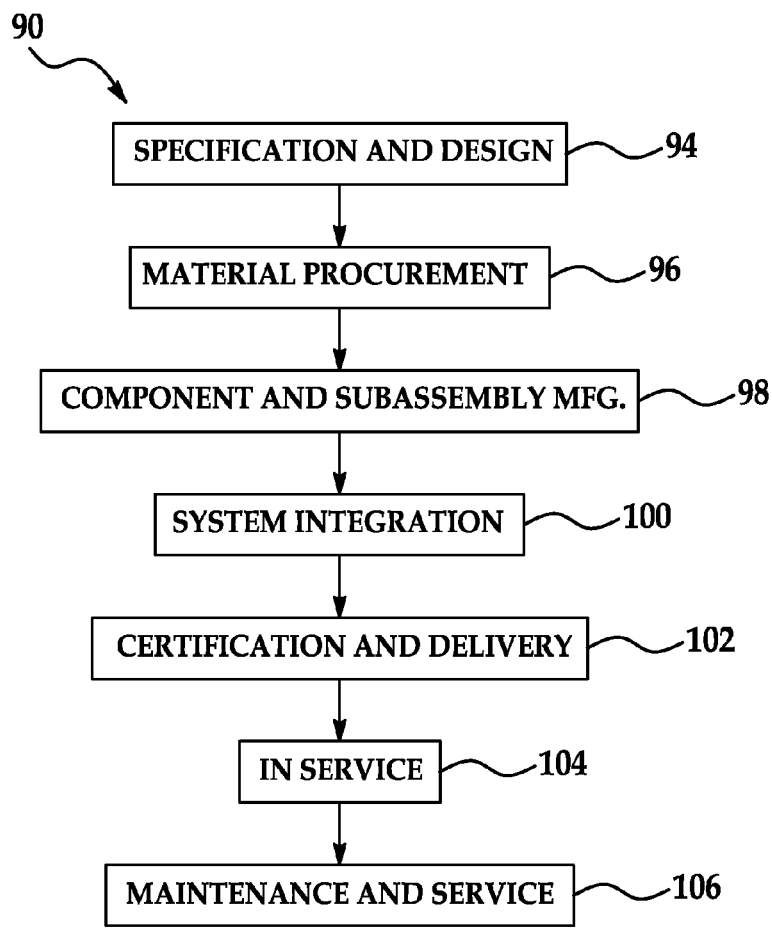
FIG. 8 is an illustration of a flow diagram of aircraft production and service methodology.
Figure 9:
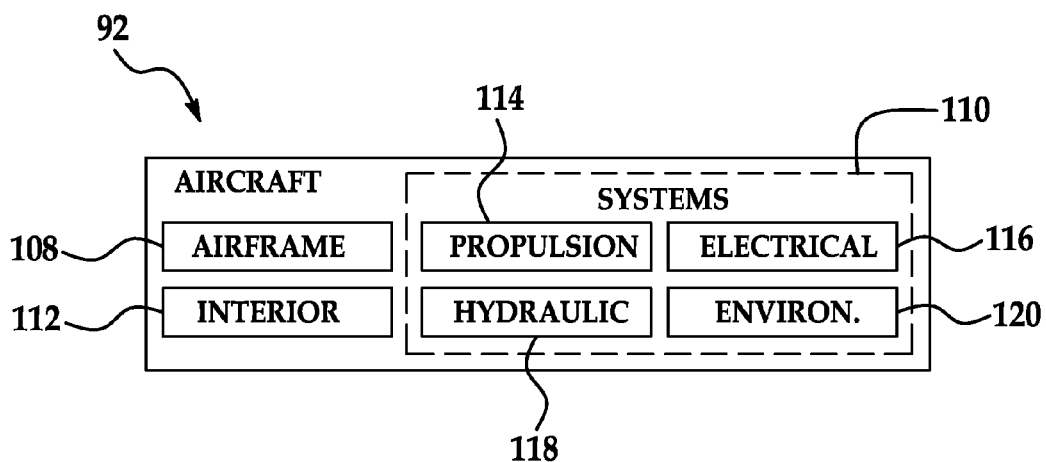
FIG. 9 is an illustration of a block diagram of an aircraft.

Embodiments of the disclosure may find use in a variety of potential applications, particularly in the transportation industry, including for example, aerospace, marine and automotive applications. Thus, referring now to FIGS. 8 and 9, embodiments of the disclosure may be used in the context of an aircraft manufacturing and service method as shown in FIG. 8 and an aircraft 92 as shown in FIG. 9. Aircraft applications of the disclosed embodiments may include, for example, a wide variety of structural and non-structural composite-to-composite and/or metal-to-composite parts and components that are bonded with adhesives. During pre-production, exemplary method 90 may include specification and design 94 of the aircraft 92 and material procurement 96. During production, component and subassembly manufacturing 98 and system integration 100 of the aircraft 92 takes place. Thereafter, the aircraft 92 may go through certification and delivery 102 in order to be placed in service 104. While in service by a customer, the aircraft 92 is scheduled for routine maintenance and service 106 (which may also include modification, reconfiguration, refurbishment, and so on).

Each of the processes of method 90 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 9, the aircraft 92 produced by exemplary method 90 may include an airframe 108 with a plurality of systems 110 and an interior 112. Examples of high-level systems 110 include one or more of a propulsion system 114, an electrical system 116, a hydraulic system 118, and an environmental system 112. Any number of other systems may be included. The disclosed method may be employed to bond parts, structures and components used in the interior 112 and in the airframe 108. Although an aerospace example is shown, the principles of the disclosure may be applied to other industries, such as the marine and automotive industries.

Systems and methods embodied herein may be employed during any one or more of the stages of the production and service method 90. For example, parts, structures and components corresponding to production process 128 may be fabricated or manufactured in a manner similar to parts, structures and components produced while the aircraft 122 is in service. Also, one or more method embodiments may be utilized during the production stages 98 and 100, for example, by substantially expediting assembly of or reducing the cost of an aircraft 92. Similarly, one or more of apparatus embodiments, method embodiments, or a combination thereof may be utilized while the aircraft 92 is in service, for example and without limitation, to maintenance and service 106.

Although the embodiments of this disclosure have been described with respect to certain exemplary embodiments, it is to be understood that the specific embodiments are for purposes of illustration and not limitation, as other variations will occur to those of skill in the art.

What is claimed:

1. A method of determining the condition of a bond surface, comprising:
   generating a wettability tension curve for the bond surface, the wettability tension curve plotted as a function of three types of surface energies, the wettability tension curve representing a range of wettings of a selected adhesive on the bond surface predicted to result in a bond joint of acceptable quality;
   measuring at least three surface energies on the bond surface related to the condition of the bond surface; and
   using the wettability tension curve to determine whether the condition of the bond surface is acceptable based on the measured surface energies.

2. The method of claim 1, wherein measuring the at least three surface energies includes:
   placing at least three reference liquids on the bond surface,
   measuring the contact angle of each of the reference liquids placed on the bond surface, and
   deriving the surface energies from the contact angle measurements.

3. The method of claim 2, wherein measuring the contact angle is performed at multiple locations on the bond surface.

4. The method of claim 2, wherein the reference liquids are selected from the group consisting of:
   distilled water,
   dimethyl sulfoxide,
   diiodomethane, and
   ethylene glycol.

5. The method of claim 1, wherein using the wettability tension curve includes determining whether the measured surface energies are within the wettability tension curve.

6. The method of claim 1, wherein generating the wettability tension curve for the bond surface uses surface tension standards for an adhesive type of the selected adhesive and surface tension standards for a substrate type of the bond surface.

7. A method of determining the condition of a bond surface, comprising:
    selecting a substrate surface and an adhesive to be applied to the selected substrate surface for making a bond joint;
    generating a database of surface tension standards for a plurality combinations of adhesives and substrate surfaces;
    placing at least three reference liquids on the selected substrate surface;
    measuring the surface tension of each of the reference liquids on the selected substrate surface;
    selecting a surface tension standard from the database corresponding to selected substrate surface and the selected bonding adhesive; and
    comparing the measured surface tension with the selected surface tension standard.

8. The method of claim 7, wherein generating the surface tension standards includes generating a 3-D wettability curve for each of the combinations of adhesives and substrate surfaces.

9. The method of claim 8, wherein generating the wettability curves includes measuring at least three surface energies for each of the combinations of adhesive and substrate surfaces.

10. The method of claim 7, wherein measuring the surface tension of the liquid on the selected substrate surface includes measuring the contact angle between the reference liquids and the selected substrate surface.

11. The method of claim 10, wherein measuring the contact angle is performed at multiple locations on the selected substrate surface.

12. The method of claim 7, wherein measuring the surface tension includes:
    measuring the contact angle of each of the reference liquids placed on the selected substrate surface.

13. The method of claim 12, wherein the reference liquids are selected from the group consisting of:
    distilled water,
    dimethyl sulfoxide,
    diiodomethane, and
    ethylene glycol.

14. A method of determining the condition of a bond surface used to predict the quality of a bond joint between an adhesive and a bond surface, comprising:
    generating a database of bond surface characteristics representing acceptable bond joint quality standards for a plurality of combinations of adhesives and bond surfaces;
    measuring at least one variable characteristic of a bond surface indicative of the condition of the bond surface;
    comparing the measured characteristic to the database characteristics; and,
    determining whether the bond surface may produce an acceptable bond joint based on results of the comparison.

15. The method of claim 14, wherein measuring at least one variable characteristic of the bond surface includes:
    placing three differing reference liquids on the bond surface, and
    measuring the contact angle between each of the reference liquids on the bond surface and the bond surface.

16. The method of claim 15, wherein measuring at least one variable characteristic of the bond surface includes deriving three surface energies of the bond surface from the measured contact angles.

17. The method of claim 14, wherein generating the database includes determining for each of the combinations of bond surfaces and adhesives the level of wetting of the adhesive on the bond surface that may produce a bond joint of acceptable quality.

18. The method of claim 14, wherein comparing the measured characteristic to the database characteristics is performed using a programmed computer.

19. The method of claim 14, wherein measuring at least one variable characteristic includes:
    placing a droplet of three differing reference liquids on the bond surface,
    measuring the contact angle between each of the droplets and the bond surface, and
    using a programmed computer to derive three surface energies of the bond surface based on the measured contact angles.

20. A method of determining the condition of a bond surface, comprising:
    generating a database of surface tension standards for a plurality of combinations of adhesives and bond surfaces;
    selecting three reference liquids from the group consisting of distilled water, dimethyl sulfoxide, diiodomethane, and ethylene glycol, wherein each of the reference liquids is capable of identifying a functional group on the bond surface;
    placing droplets of three of the selected reference liquids at multiple locations on the bond surface;
    measuring the contact angle between each of the droplets and the bond surface;
    deriving from each of the contact angle measurements three surface energies at each of the locations on the bond surface;
    selecting a surface tension standard from the database corresponding to the combination of the adhesive and the bond surface;
    determining the surface tension of the adhesive applied to the bond surface using the derived surface energies; and
    comparing the determined surface tension with the selected surface tension standard.

* * * * *